(12) United States Patent
Smith et al.

(10) Patent No.: US 7,676,075 B2
(45) Date of Patent: Mar. 9, 2010

(54) QUANTITATIVE SINGLE IMAGE-BASED MAGNETIZATION TRANSFER WEIGHTED IMAGING USING AN INTER-SUBJECT NORMALIZATION REFERENCE WITHIN THE IMAGE

(75) Inventors: Seth Smith, Baltimore, MD (US); Xavier Golay, Vista Park (SG); Peter C. M. van Zijl, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 175 days.

(21) Appl. No.: 11/660,361

(22) PCT Filed: Aug. 17, 2005

(86) PCT No.: PCT/US2005/029284

§ 371 (c)(1),
(2), (4) Date: Nov. 2, 2007

(87) PCT Pub. No.: WO2006/023581

PCT Pub. Date: Mar. 2, 2006

(65) Prior Publication Data

US 2008/0199061 A1  Aug. 21, 2008

Related U.S. Application Data

(60) Provisional application No. 60/602,158, filed on Aug. 17, 2004.

(51) Int. Cl.
*G06K 9/00* (2006.01)
(52) U.S. Cl. .................................................... 382/131
(58) Field of Classification Search ................. 382/128, 382/131; 324/307, 309; 600/410
See application file for complete search history.

(56) References Cited

U.S. PATENT DOCUMENTS

| 5,846,197 A | 12/1998 | Edelman .................... 600/419 |
| 6,717,405 B2 | 4/2004 | Alsop ......................... 324/306 |
| 2002/0188190 A1* | 12/2002 | Kassai et al. ................ 600/410 |

* cited by examiner

*Primary Examiner*—Andrew W Johns
(74) *Attorney, Agent, or Firm*—McKenna Long & Aldridge LLP

(57) ABSTRACT

Disclosed is a system and method for generating quantitative imagery of demyelination in the spinal cord. The method includes acquiring a magnetization transfer weighted (MTw) MR image of the spinal column, identifying a reference region of interest within the image corresponding to cerebrospinal fluid (CSF), averaging the signal intensity corresponding to the reference region of interest, and computing a ratio, on a voxel-by-voxel basis, of the signal intensity of each voxel by the averaged reference signal intensity. In doing so, normalized MTw images are obtained such that detrimental artifacts such as motion-induced errors, coil loading, and RF coil sensitivity variations are obviated.

15 Claims, 8 Drawing Sheets

QUANTITATIVE SINGLE IMAGE-BASED MAGNETIZATION TRANSFER WEIGHTED IMAGING USING AN INTER-SUBJECT NORMALIZATION REFERENCE WITHIN THE IMAGE

REFERENCE WITHIN THE IMAGE

This application claims the benefit of U.S. Provisional Patent Application No. 60/602,158, filed on Aug. 17, 2004, which is hereby incorporated by reference for all purposes as if fully set forth herein.

Research and development related to the invention disclosed below was funded in part through a grant from the National Institutes of Health/National Institute for Biomedical Imaging and Bioengineering, grant no. EB00991-01.

BACKGROUND OF THE INVENTION

1. Field of the Invention

The present invention involves the field of Magnetic Resonance Imaging (MRI). Particularly, the present invention involves the use of MR signal information from a reference substance identified within an MR image to provide quantitative Magnetization Transfer weighted (MTw) images. More particularly, the present invention involves the use of MR signal corresponding to cerebrospinal fluid (CSF) as a reference to provide quantitative MTw images of the spinal cord.

2. Discussion of the Related Art

Certain neurological diseases, such as Adrenomyeloneuropathy (AMN), Multiple Sclerosis (MS), genetic leukodystrophies, and Amyotrophic Lateral Sclerosis (ALS), involve a breakdown of the myelin sheath present in white matter of central nervous system tissue. Such demyelination can become apparent within the spinal cord before becoming apparent in the brain, and before becoming detectable via conventional (T1w, T2w) MRI techniques. As such, early diagnosis of these diseases may be achieved by identifying and quantitatively assessing the breakdown of myelin found in white matter within the spinal cord.

In addition to diagnosing demyelinating diseases, quantitative assessment of the breakdown of myelin within the spinal cord may be used to determine the effect of trauma to the spinal cord.

Magnetization Transfer Ratio (MTR) imaging is a known MRI technique that is often used for imaging and quantifying the extent of white matter diseases in the brain and spinal cord. MTR imaging involves acquiring two MR images, one with and one without off-resonance (with respect to water) radiofrequency (RF) saturation of the solid-like, macromolecular proton species (or solid phase protons, hereinafter "solid component") present in the target tissue. The image acquired in the absence of RF saturation is referred to as the reference image, while the image acquired with RF saturation is referred to as the saturation image or MT weighted (MTw) image. As used herein, "imagery" may refer to a single image, or multiple images taken at different times or corresponding to different characteristics, such as RF frequency.

Tissue containing solid-like macromolecular proton species, i.e., solid components, within the target tissue can be preferentially saturated by an off-resonance (different irradiation frequency with respect to the water frequency) RF pulse. This so-called magnetization transfer (MT) prepulse or preparation pulse partially saturates the solid proton pool, and this saturation is subsequently transferred to free water protons, which are imaged by conventional MRI techniques. White matter has a greater density of solid-like macromolecular protons than grey matter (due to its large proportion of myelin) and thus will transfer more saturation to the free water protons, leading to a greater magnetization transfer (MT) effect. Computing the voxel-by-voxel ratio of the two images (saturation over reference) provides a quantitative assessment, of the sensitivity of the MT effect in different tissues contributing to the image, e.g. white matter vs. grey matter. MTR imaging is discussed in further detail in U.S. Pat. No. 5,050,609 to Balaban et al., which is incorporated by reference as if fully disclosed herein.

As mentioned above, MTR images are obtained by performing a reference scan and a saturation scan. A normalized signal response is then computed according to the following relation:

$$\frac{M_z(\omega)}{M_o} = 1 - MTR \qquad (1)$$

where $M_z(\omega)$ is the signal corresponding to a given voxel taken during the saturation scan at the irradiation frequency $\omega$; $M_o$ is the signal corresponding (ideally) to the same voxel taken during the reference scan; and MTR refers to the Magnetization Transfer Ratio of the target tissue within the voxel.

Problems associated with the related art include the following. First, motion induced errors between the reference scan and the saturation scan limit the quality of the computed MTR. Second, coil loading effects of the MR scanner affect the repeatability of typical MTw images for a given patient, therefore, while the extent of demyelination may be determined for a given patient at a single time point using MTw imaging, it is generally not possible to quantitatively track the progression of the disease for a given patient with MTw imaging alone.

Motion control-induced errors result from the fact that $M_z(\omega)$ and $M_o$ are taken from two different images that are acquired at different times. Since these two signals are acquired during two different scans that are temporally separated, the voxels must be co-registered, which results in uncertainty in their correspondence if the co-registration is not perfect. Any motion of the target tissue between these scans reduces the precision of the Magnetization Transfer Ratio, and thus decreases the Signal to Noise Ratio (SNR) of the resultant MT image and dilutes the quantitative assessment of the tissue MT effect. Out of plane motion between image acquisitions is particularly problematic in that image manipulation cannot register voxels corresponding to tissue regions that have moved into, or out of, the image plane between image acquisitions.

Related art solutions that attempt to compensate for motion of the target tissue include sophisticated image registration algorithms, which use feature recognition to map one image onto another so that a voxel-by-voxel MTR may be computed with some acceptable precision. As such, related art motion compensation techniques generally improve the quality of MTR images of the brain. Although MTR assessment is quite robust with regard to the brain, it has not been very successful in assessing the spinal cord.

There are problems associated with the related art motion compensation techniques, which make quantitative assessment of the spine prohibitively difficult. For example, the spinal cord has much smaller (spinal cord diameter at cervical vertebra C2~1.5 cm) structures than the brain. The dorsal and lateral columns of the cervical spinal cord are of particular interest as they carry vibration sensitivity and motion impulses to and from the extremities, respectively. As such, obtaining precise MTR images of these regions is important in diagnosing many of the aforementioned diseases. However, discriminating white and grey matter structures within the spinal cord generally requires a transverse spatial resolution between 0.5 mm and 2 mm. Such high-resolution imaging increases the motion sensitivity. Given the smaller features of the spinal cord, such as the spinal cord tracts which are separated by the sub-centimeter grey matter horns, related art motion compensation techniques have been found to often be inadequate for registering two sequentially acquired MR images. This makes related art MTR imaging of the spinal cord at spatial resolutions required for early visualization of demyelinating diseases prohibitively unreliable. As such, related art applications of MTR imaging of the spinal cord are generally limited to identifying large scale effects of demyelinating diseases by imaging large inflammatory lesions within the spinal cord, and generally require a priori information pertaining to the location and etiology of the particular disease.

Second, it is possible to obtain high resolution, high SNR MTw images in the spinal cord, but MTw imagery alone is confounded by coil loading effects of the MR scanner making MTw imaging qualitative, but not quantitative. Any RF coil within an MR scanner has a gain pattern, which results in a position-dependent sensitivity. As such, repeatability between successive MTw images requires that the target tissue be located at the same location within the RF coil's gain pattern for each image acquisition, which is unlikely. Further, coil loading (electromagnetic interaction between the patient and the RF coil) limits the repeatability of successive MTw image acquisition. This is because the sensitivity of the MR scanner, and thus the resultant MTw values, changes temporally, which prevents quantitative inter-MTw image comparison for a given patient, unless properly normalized.

For at least these reasons, there is a strong need for high-SNR motion-insensitive MT imagery, which is repeatable, which may be quantitatively assessed with respect to a control subject, and which has sufficient spatial resolution to discern white matter structures and to separate these structures from the surrounding grey matter within the spinal cord.

SUMMARY OF THE INVENTION

Accordingly, the present invention is directed to quantitative single image-based magnetization transfer weighted (MTw) imaging using an inter-subject normalization reference within the single image that substantially obviates one or more of the problems due to limitations and disadvantages of the related art.

An advantage of the present invention is that it provides a more precise visualization and quantitative assessment of loss of solid components within white matter.

Another advantage of the present invention is that it better enables early quantification of myelin loss in several white matter diseases in the spinal cord and can thus follow disease progression at an early stage of the disease.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, a method is provided for quantifying loss of macromolecular components in tissue, wherein the method comprises acquiring an MTw image of the tissue, the MTw image having a plurality of voxels, wherein each voxel has a corresponding MR signal; identifying a reference region of voxels within the plurality of voxels, wherein the region of voxels corresponds to a reference material having a minimal magnetization transfer effect; computing a reference MR signal corresponding to the region of voxels; and computing a normalized MT weighted image, based on the ratio of the MTw image and the reference MR signal.

In another aspect of the present invention, an MRI system is provided, which comprises a main magnet; a gradient coil; an RF coil; and a computer having a computer readable medium encoded with a program for acquiring an MTw image of the tissue, the MTw image having a plurality of voxels, wherein each voxel has a corresponding MR signal; identifying a reference region of voxels within the plurality of voxels, wherein the region of voxels corresponds to a reference material having a minimal magnetization transfer effect; computing a reference MR signal corresponding to the region of voxels; and computing an MTCSF image, based on the MR image and the reference MR signal.

In another aspect of the present invention, a method for quantifying demyelination in a spinal cord is provided, which comprises acquiring an MTw image of the spinal cord, the MTw image having a plurality of voxels, wherein each voxel has a corresponding MR signal; identifying a reference region of voxels within the plurality of voxels, wherein the region of voxels corresponds to cerebrospinal fluid; computing a reference MR signal corresponding to the region of voxels; and computing a normalized MT weighted image, based on the ratio of the MTw image and the reference MR signal.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE ILLUSTRATED EMBODIMENTS

According to the present invention, an internally-referenced MTw image is generated, which is hereinafter referred to as an MTCSF image. An MTCSF image is generated on a voxel-by-voxel basis from a single acquired MTw image according to the following relation:

$$MTCSF = \frac{M_z(\omega)}{\langle CSF \rangle_{ROI}} \quad (2)$$

where MTCSF is the magnetization transfer ratio using CSF as the internal intensity reference; $M_z(\omega)$ is the MR signal acquired at the RF saturation frequency, $\omega$, wherein $M_z$ corresponds to the signal intensity in a given voxel within the single image; $\langle CSF \rangle_{ROI}$ is the MR signal intensity averaged over a region of interest (ROI) corresponding to cerebrospinal fluid (CSF) and normalized per voxel. Cerebrospinal fluid serves as an effective reference because it has negligible magnetization transfer effect, which is common across subjects, and is temporally invariant. Accordingly, instead of performing a separate reference scan and registering the saturation image to such a reference image, a quantitative normalized MTw image is generated by extracting the saturation and reference information from a single image. By extracting the saturation and reference information from a single image, imprecision that generally results from merging data associated with multiple images acquired over a period of time, such as motion-induced imprecision in image registration and variations in RF coil response, are obviated. Further, because the negligible magnetization transfer properties of CSF is common across subjects and is temporally invariant, CSF provides a reference that enables inter-subject quantitative comparison as well as quantitative comparison between successive MTCSF images acquired of a single patient.

As used herein, the term "voxel" may refer to either of the terms voxel and pixel.

An MTCSF image generated by the present invention provides a quantitative image of the magnetization transfer effect, which corresponds to the spatial distribution of solid matter components within the imaged tissue. MTCSF imagery provides for discrimination between white matter and grey matter within the spinal cord independently of coil loading and B1 receptivity effects. Accordingly, MTCSF imagery enables the quantitative assessment of white matter tracts within the spinal cord before the SD, T2 (or T2*), T1 related effects of demyelination, (which are discernable using conventional MRI) are detected.

Figure 1:
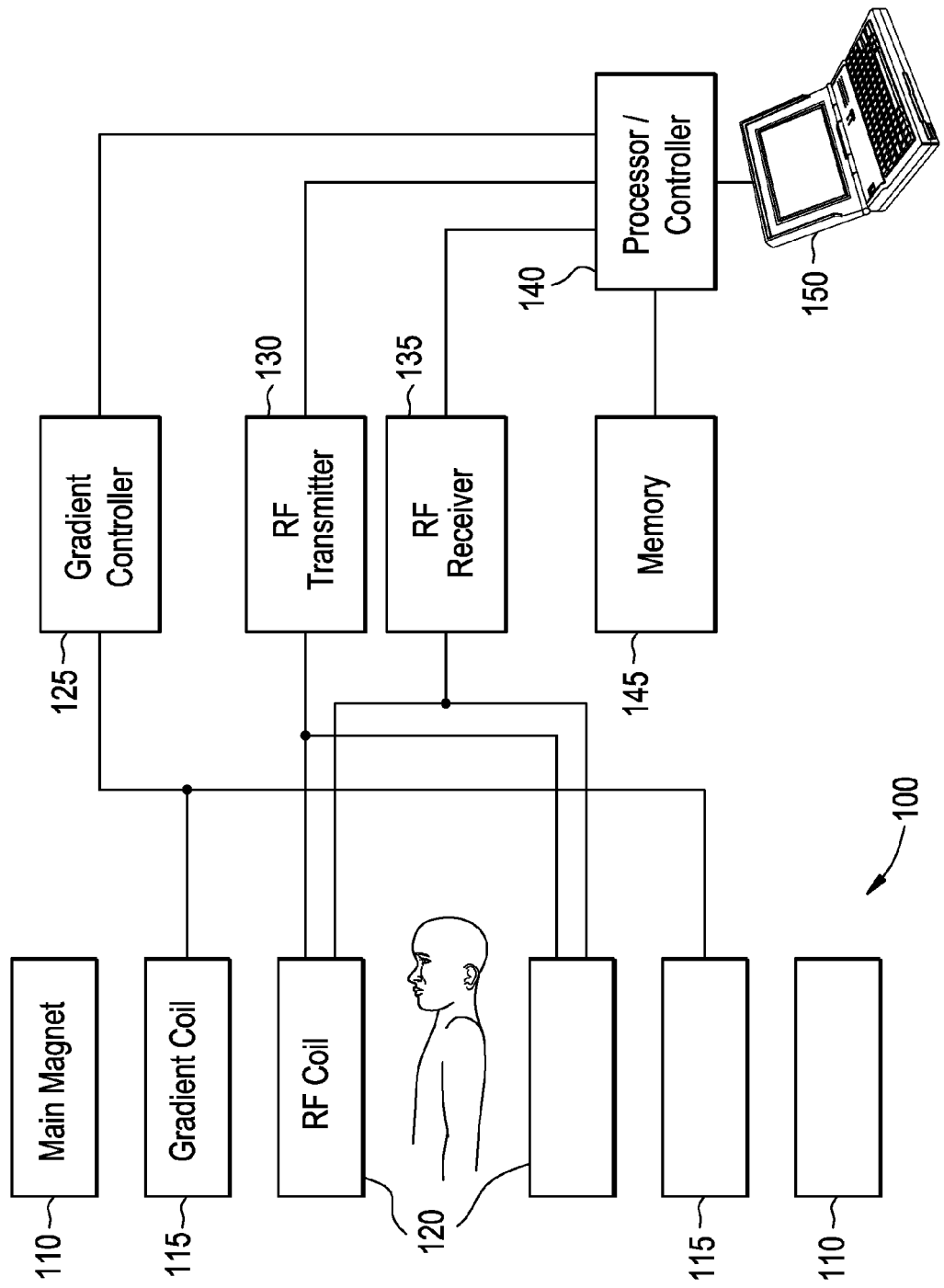
FIG. 1 illustrates an exemplary MRI system for generating MTw images needed for the present invention.

FIG. 1 illustrates an exemplary system 100 for providing MTw images according to the present invention. System 100 includes a main magnet 110; a gradient coil 115; an RF coil 120; a gradient controller 125; an RF transmitter 130; and an RF receiver 135. System 100 further includes a processor/controller 140 having a memory 145 and a user interface 150. The RF coil 120 may include two coils: one for transmitting and one for receiving. All of these components within system 100 may be standard equipment found in commercial MRI systems like those available from manufacturers such as Philips Medical Systems, GE Medical Systems, and Siemens Medical Systems, and other manufacturers.

The processor/controller 140 may include one or more computers, which may be co-located, may include one or more remote computers connected over a network, and/or may include embedded processors within other components associated with system 100. The memory 145 may be integrated into the processor/controller 140 or may include distributed components, such as remote databases. The memory 145 is encoded with programs for operating the system 100, including software for implementing the processes according to the present invention (hereinafter "the software"). The software may be stored in a separate memory device within memory 145 or may be integrated into memory components provided within a commercial MRI system.

In a particular embodiment of the present invention, system 100 includes a 1.5-T Philips Intera-NT system (Philips Medical Systems), which is equipped with a high performance gradient system (60 mT/m amplitude in three combined directions and 120 T/m/s slew rate. In this embodiment, the RF coil 120 includes a quadrature body coil for RF transmission, and a two-element phased array coil (FLEX-M coil) for reception. However, it will be readily apparent to one of ordinary skill that other MRI systems, including inter alia different field strengths for the main magnet 100 and different configurations of RF coil 120, may be used.

Figure 2:
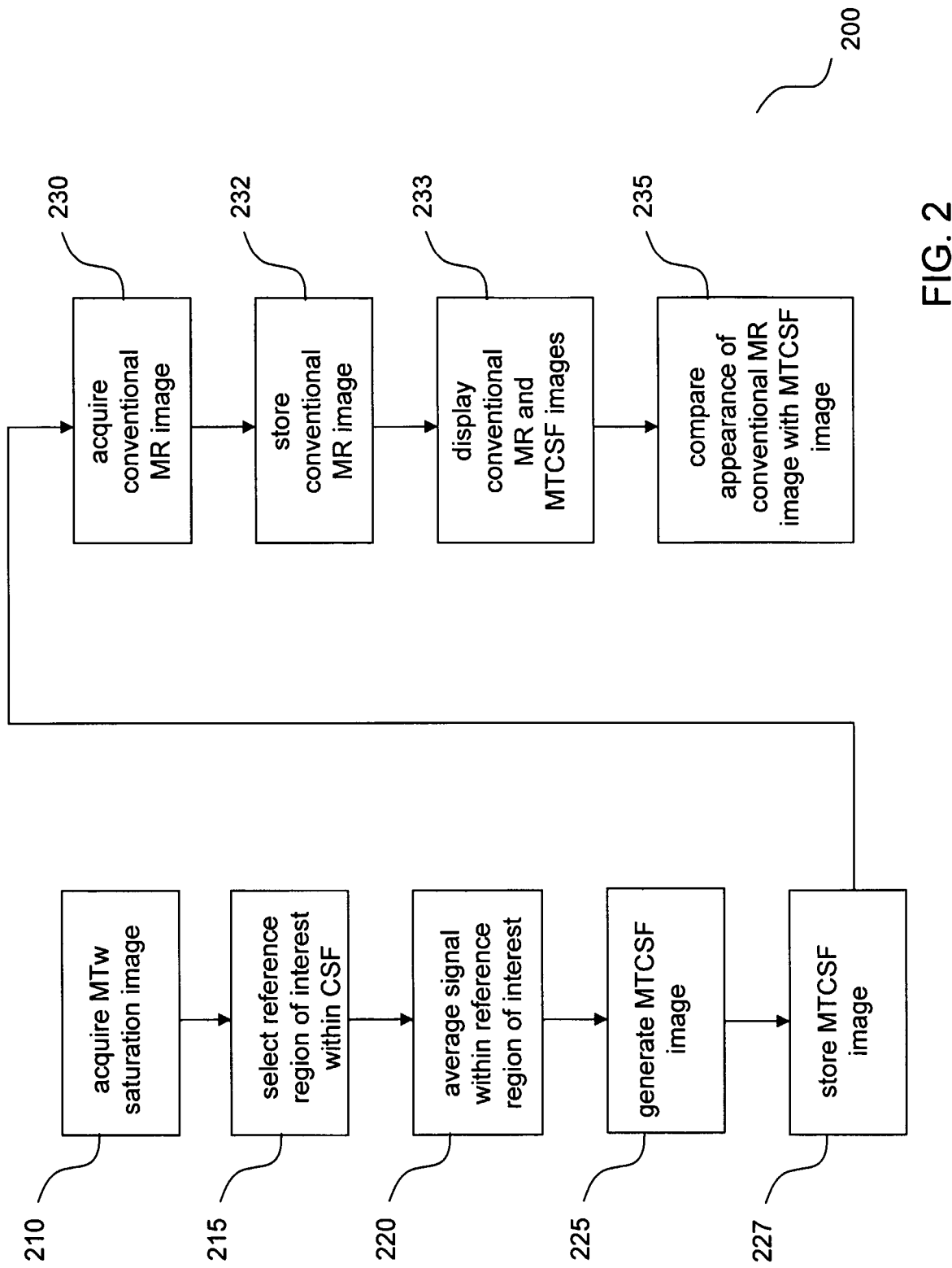
FIG. 2 illustrates an exemplary process for generating quantitative MTw images according to the present invention.

FIG. 2 illustrates an exemplary process 200 for providing MTw imagery according to the present invention. Process 200 includes two sub-processes. The first sub-process, which includes steps 210-227, involve generating an MTCSF image according to the present invention. The second sub-process is optional. The second sub-process, which includes steps 230-235, involves comparing the MTCSF image with a conventional MR image. Comparing the MTCSF image with a conventional image would provide the ability to determine the extent of demyelination (identified in the MTCSF image) and determine if atrophy, inflammation, etc., (identified in the conventional MR image) are present in the same regions. In doing so, early onset of demyelinating diseases may be identified.

Process 200, which is implemented by the software, may be integrated into a standard MRI clinical procedure. In doing so, early detection of demyelinating diseases may be a standard feature of MRI clinical procedures.

In step 210, system 100 acquires an MTw saturation image that will later be processed into an MTCSF image according to the present invention. In acquiring an MTw saturation image, the software issues commands to the gradient controller 125, the RF transmitter 130, and the RF receiver 135 to provide an MTw gradient echo pulse sequence. Such a pulse sequence provides a MR signal whereby the cerebrospinal fluid (CSF) typically appears bright, white matter appears dark, and grey matter is at some medial intensity. In a particular embodiment of the present invention, the pulse sequence is a 3D-Gradient Echo pulse sequence (TR/TE/α=50 ms/13 ms/7°) with a five lobed, sinc-shaped MT prepulse of 15 ms, and an RF offset of 10 kHz. However, it will be readily apparent to one of ordinary skill that the particular parameters corresponding to the pulse sequence will vary depending on the characteristics of the MRI system 100, and that many variations to the above pulse sequence are possible and within the scope of the invention.

Certain commercial MRI systems have the capability to do real time signal averaging (in k-space) to increase SNR. The software may take advantage of this feature by issuing commands to the RF transmitter 130 and the RF receiver 135 to acquire and average multiple MR signals per voxel per scan. Although this increases SNR, it lengthens the time required to acquire an image.

The length of time needed to acquire a line (or lines) of k-space (referred to as the repetition time, TR) should be kept sufficiently short so that effect of flow of the CSF is minimized during the duration of the scan. During a given scan, when an image is being acquired, the CSF excited by the readout RF pulse continuously moves out-of-plane in the longitudinal direction. As the duration of the scan increases, more of the excited CSF moves out of the field of view, and the CSF that was not excited by the readout RF pulse moves into the field of view. This CSF motion in and out of the field of view can increase the CSF signal intensity (referred to as inflow effect) used as a reference in computing the MTw image. Accordingly, it is possible to mitigate the inflow effect by decreasing the repetition time, which in turn decreases the duration of the scan. In general, it is advisable that the repetition time TR is kept below 100 ms to safely obviate the effects of CSF inflow, but it is not a necessity as the accuracy of MTCSF may be maintained with a modest flow effect.

The acquired MTw image includes a plurality of MR signals, $M_z$, one per voxel. The software stores the $M_z$ data values corresponding to the image, or images if multiple image slices are acquired.

In step 215, the software selects a reference region of interest (ROI) within each acquired image wherein the ROI contains only signal from CSF. Because step 210 employs a T2* weighted pulse sequence, CSF appears bright in the image, and may be easily identified. Optimally, the ROI is selected such that each voxel within the ROI solely corresponds to CSF, and thus partial volume effects are obviated.

Further, in accordance with step 215, the software identifies voxels corresponding to the CSF by using one or more image processing algorithms that are known to the art to recognize substantially uniform bright regions that correspond to CSF. The software may determine a single reference region of interest (ROI), which includes a contiguous region of CSF voxels. Alternatively, the software may identify multiple such ROIs within the image. The software may use other image processing techniques to identify an ROI, such as recognizing features such as the spinal canal to determine a ROI. Further, the software may include user interaction to select the ROI, through the user interface 150. It will be readily apparent to one of ordinary skill that multiple software approaches to identifying one or more ROI are possible and within the scope of the invention.

Figure 3:
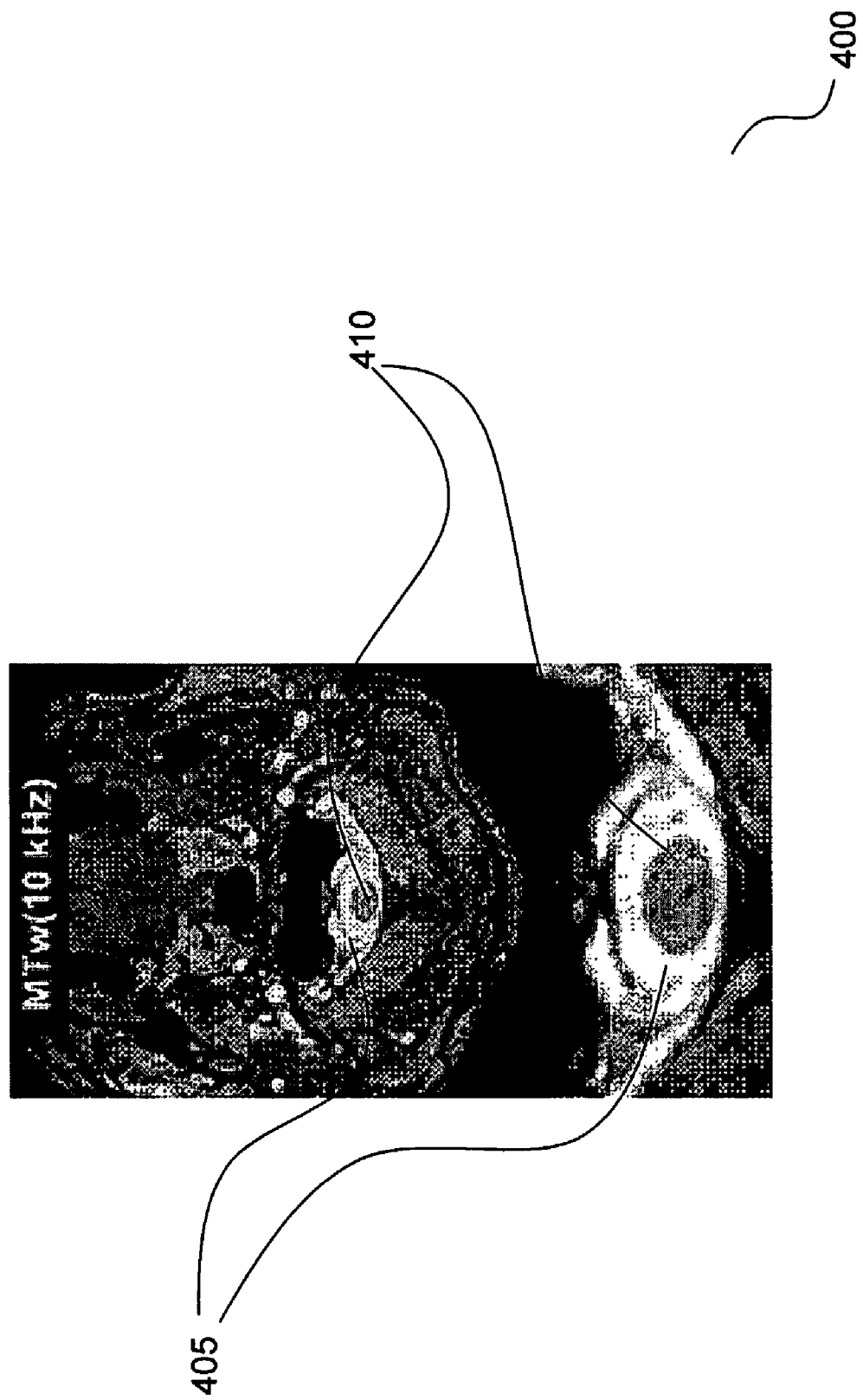
FIG. 3 shows an exemplary axial MTCSF image of the neck, including the cerebrospinal fluid, spinal cord, and spinal column.

FIG. 3 shows an MTw image 400 of a spinal column according to step 210 of the present invention. Shown in image 400 is the CSF 405, within the spinal canal, and the spinal cord 410. As is apparent from FIG. 3, the MTw image acquired in accordance with step 210 clearly shows the CSF 405 and distinguishes it from the other image features. This permits the software to select the ROI within the CSF according to step 215.

The software may also provide a configuration setting, whereby the degree of homogeneity of the CSF signal values within the ROI may be predetermined. This would generally involve a tradeoff between the number of CSF signal values that are averaged to compute $<CSF>_{ROI}$, and the standard deviation of the average. In general, by adjusting the degree of homogeneity, the size of the ROI may change accordingly. It will be apparent to one of ordinary skill that various software architectures for configuring the software as such are known and can be developed that are within the scope of the invention.

In step 220, the software averages the signal corresponding to each voxel within the reference ROI to compute $<CSF>_{ROI}$. If the software identifies more than one ROI step 215, the software averages the total number of voxels across all the combined ROIs. The software then stores the resulting average in memory.

Step 220 may have an additional sub-step whereby outlier CSF signal values within the ROI are identified and discarded. Algorithms for outlier identification are known to the art and within the scope of the invention.

In step 225, the software generates an MTCSF image. In doing so, the software retrieves the MR signal data values $M_z$ that were stored in step 210, retrieves the $<CSF>_{ROI}$ computed in step 220, and computes the MTCSF values according to equation (2) above.

In step 227, the software stores the MTCSF values in memory 145. The software may also display the MTCSF image on the user interface 150.

In step 230, the software issues commands to acquire one or more conventional MR images, which may include spin density, T2- (or T2*), and T1-weighted images, as might be done in a typical clinical MRI examination.

In step 232, the software stores the conventional MR image in memory 145.

In step 233, the software displays the MTCSF and conventional MR images on user interface 150.

Figure 5A:
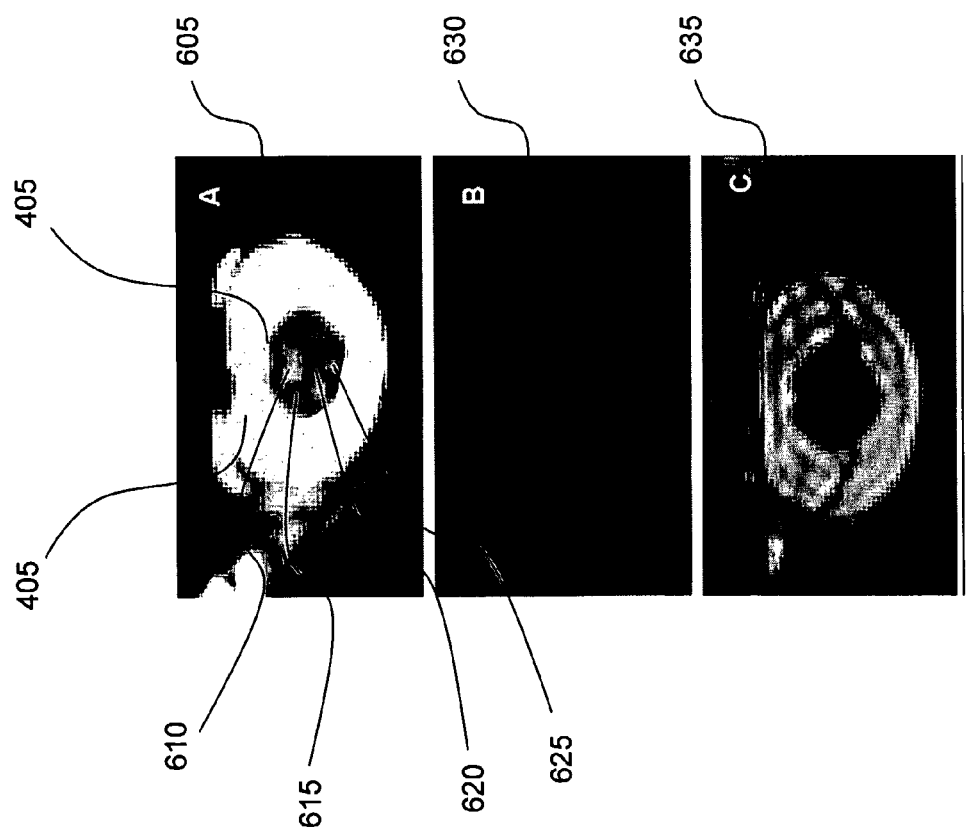
FIG. 5A shows an exemplary MTCSF image in AMN as compared to conventional T1w and T2w images, which may be acquired as part of a standard clinical MRI procedure.

FIG. 5A shows an exemplary MTCSF image 605, along with T1w (T1-weighted) image 630, and T2w (T2-weighted) image 635 in the non-inflammatory, demyelinating disease, AMN, whereby T1w and T2w images are acquired in step 230 as part of the conventional MRI examination. Images 605, 630, and 635 are example images of what the software would display in step 233.

Each voxel in the MTCSF image 605 has a value equal to the corresponding MTCSF value computed according to equation 2. The software may have features that provide the clinician (through user interface 150) to select a voxel, or regions of voxels, and see the MTCSF value corresponding to the selected voxel or voxels.

The MTCSF image 605 includes the CSF 405 and the spinal cord 410. Features visible within the spinal cord 410 in MTCSF image 605 include a "butterfly" pattern of grey matter 610, the right lateral column 615 (also left lateral column on the contralateral), and the dorsal column 620. Note that the MTCSF image 605 provides contrast sufficient to discern these features, which are not discernable in respective conventional T1w and T2w images 630 and 635. Exemplary MTCSF image 605 shows a region of hyperintensity 625 within the white matter in the dorsal column 620. The hyperintensity region 625 is a result of demyelination of the white matter in the dorsal column 620 reflective of AMN.

The software may store MTCSF (in step 227) and conventional MR images (in step 232) pertaining to a single patient over multiple clinical MR sessions, and may do so for multiple patients. In step 233, the software may display multiple MTCSF images and conventional MR images acquired in different clinical MRI sessions.

Figure 5B:
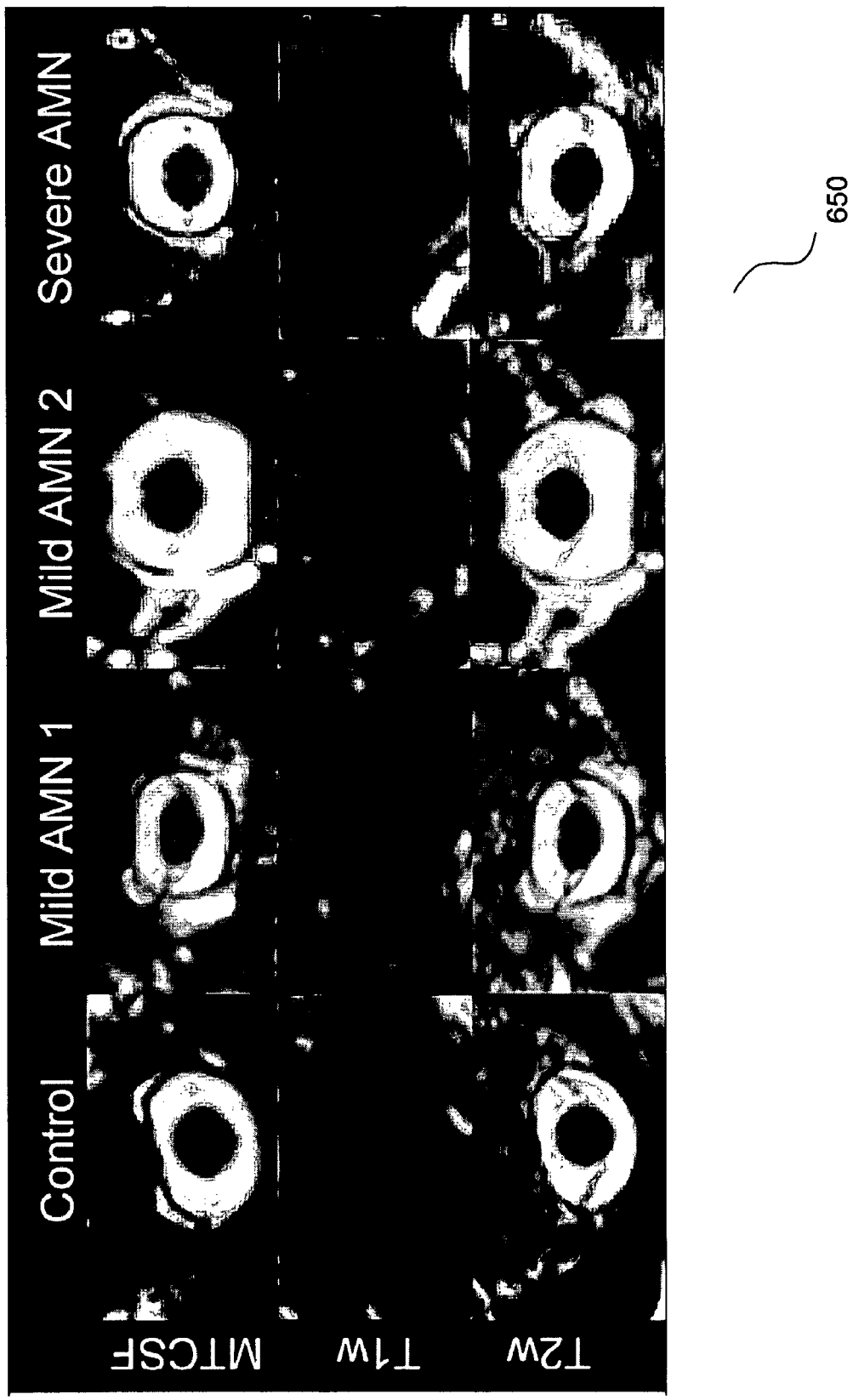
FIG. 5B shows an exemplary set of MTCSF images (and conventional T1w and T2w images), which may be compared with a control image set (MTCSF, T1w, T2w) to identify white matter abnormalities according to the present invention.

FIG. 5B shows exemplary MTCSF images 650 of a control subject as well as subjects with varying degrees of adrenomyeloneuropathy (AMN), as may be displayed in step 233. In displaying multiple images, as shown in FIG. 5B, a clinician may be able to assess the development of demyelination, or compare demyelination of a given patient with a control subject.

In step 235, the software compares the conventional MR image with the MTCSF image. Comparing the MTCSF image with a corresponding conventional MR image may reveal demyelination, by identifying the reduction of solid components in white matter (in the MTCSF image) that is independent of T1, T2, and spin density changes, which are consistent with other forms of damage to the white matter, such as atrophy, inflammation, and acute trauma. The conventional MR image is used to identify the T1, T2 or T2*, and spin density effects.

Figure 6:
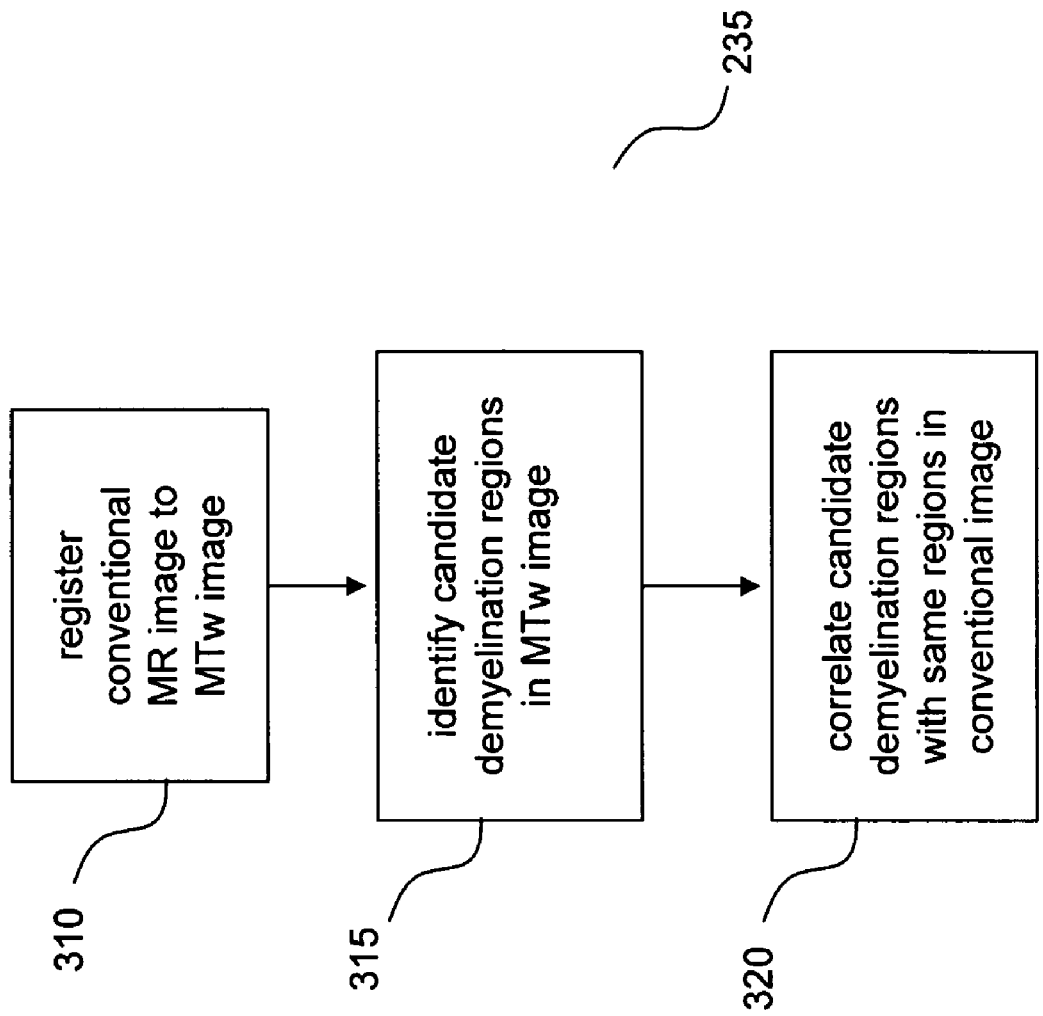
FIG. 6 illustrates an exemplary process for comparing MTw images with conventional (T1w and T2w) MR images.

FIG. 6 illustrates an exemplary process for implementing the step of comparing the MTCSF and conventional MR images. As illustrated, step 235 includes sub-steps 3102-320.

In sub-step 310, the software co-registers the MTCSF image and the conventional MR image. The software may do this using image registration algorithms, such as multi-degree-of-freedom rigid-body transformation techniques provided in many software packages, that are known to the art.

In sub-step 315 candidate regions of demyelination are identified. This may be done by the software, whereby the MTCSF image is compared with a control image to identify the candidate regions within the MTCSF image that have white matter. Any discrepancies (i.e., differences) between the MTCSF image and the control images, may indicate a loss of white matter consistent with demyelination, dysmyelination, or similar etiologies. The software may have configurable thresholds that determine if a discrepancy is sufficient to be a candidate for pathology.

Figure 4:
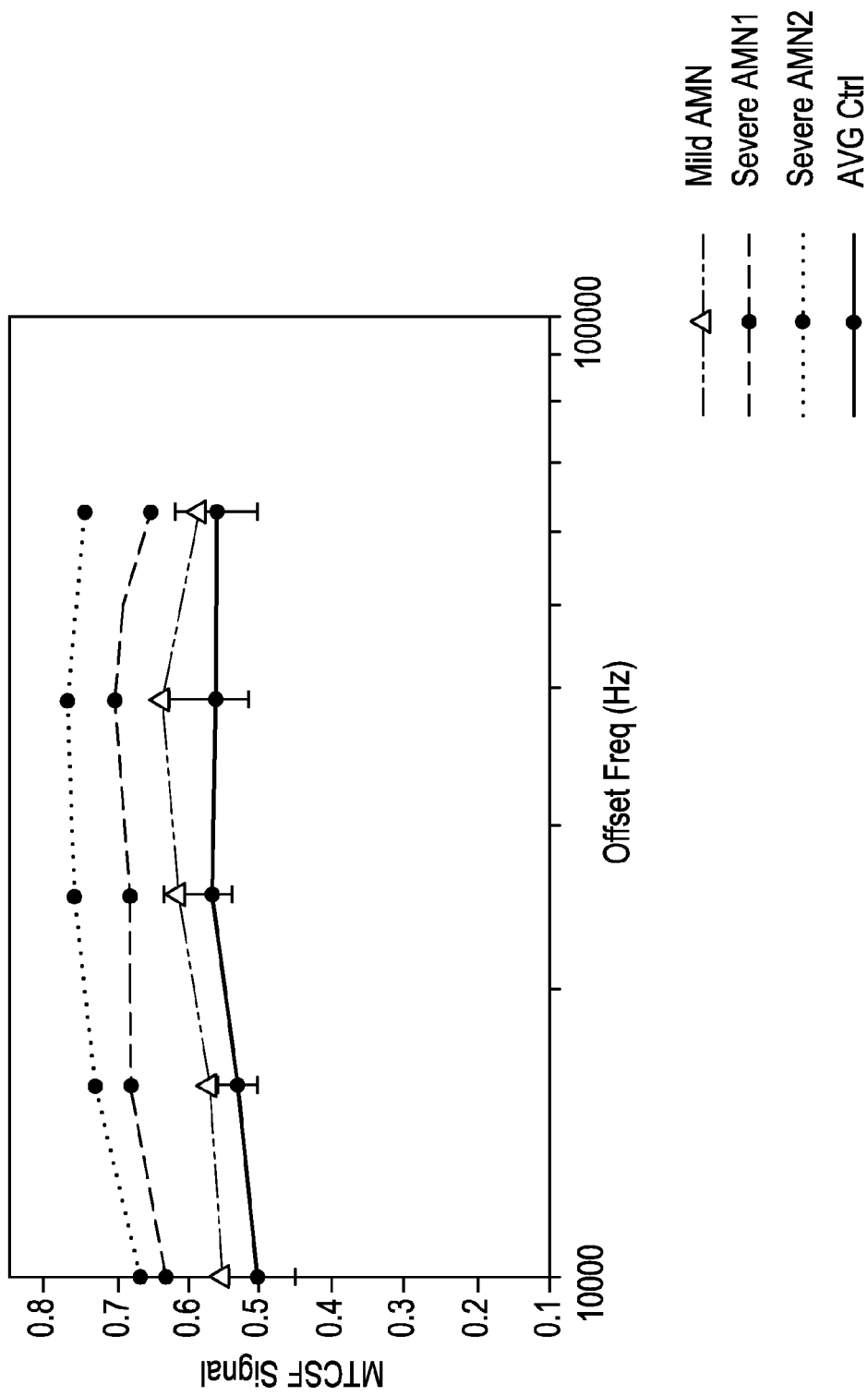
FIG. 4 illustrates an exemplary set of curves comparing dorsal column MTCSF at C2 with varying states of white matter pathology.

FIG. 4 illustrates an exemplary set of MTCSF curves for a region of interest in the dorsal column at the level of C2 as a function of RF offset frequency for expected MTCSF values for normal white matter (AVG Ctrl) and different degrees of demyelination corresponding to different states of adrenomyeloneuropathy (AMN, a non-inflammatory, demyelinating neurodegenerative disease). In an embodiment of the present invention in which the RF excitation frequency is 10 kHz, the thresholds may be set as follows: an MTCSF value of about 0.5 corresponds to normal white matter; an MTCSF value of about 0.55 corresponds to demyelination consistent with mild AMN; an MTCSF value of about 0.63 corresponds to severe AMN1; and an MTCSF value of about 0.67 corresponds to severe AMN 2. The data values corresponding to FIG. 4 may be stored in memory 145 as a look-up table, which may be referenced to correlate MTCSF with varying states of white matter pathology.

In sub-step 320, the software correlates the voxels within the candidate demyelination regions identified in step 315 with the corresponding voxels in the conventional MR image. In doing so, the software retrieves the T1, T2 or T2*, and/or spin density data of the corresponding voxels of the conventional MR image and compares this data with known T1, T2, and/or spin density effects due to conditions such as atrophy, inflammation, trauma, etc.

In general, a candidate region showing signal changes indicating myelin loss, which does not show any T1, T2, or spin density effects due to atrophy or inflammation in the conventional MR image, may indicate the early stages of any of the demyelinating diseases listed above or any other diseases exhibiting myelin loss. This can also be done when comparing MTw imaging with such conventional imaging.

In an alternate embodiment of the present invention, multiple MTCSF images may be generated in the form of longitudinal "slices." By acquiring multiple MTCSF image slices, changes in demyelination as along the spinal cord may be quantified, and localized regions of demyelination may be pinpointed. In such a case, subsequent processing in process 200 is done on each image slice independently.

In step 210, image slices may be acquired between, for example, C1 and C3 along the spinal cord.

If the MTCSF image slices are to be compared with similar imagery corresponding to different subjects, then step 210 may include an interpolation sub-step, in which each subject has images taken along the same locations along the spinal cord, and thereby differences in subjects' neck length may be compensated. For example, images may be linearly interpolated to fit a pre-selected number of slices at an average distance from the nerve roots of C1 to the nerve roots of C3.

In step 230, multiple conventional images may be acquired along the same slices taken in step 210.

The software may provide the capability to display multiple MTCSF values (one per image slice) corresponding to a feature or region selected by the clinician via the user interface 150. In doing so, the clinician may observe and quantify the degree of tissue abnormality as a function of slice position along the patient's spinal cord. Such a feature may help identify the particular disease causing the pathology. For instance, adrenomyeloneuropathy (AMN) is a non-inflammatory diffuse pathology that generally shows consistent demyelination along the spinal cord. Other diseases, such as MS and ALS, show demyelination that is concentrated in particular locations along the spinal cord. Accordingly, by acquiring multiple MTCSF image slices, it may be possible to identify the region along the spinal column showing the greatest amount of damage, and to possible identify the particular disease.

Figure 7:
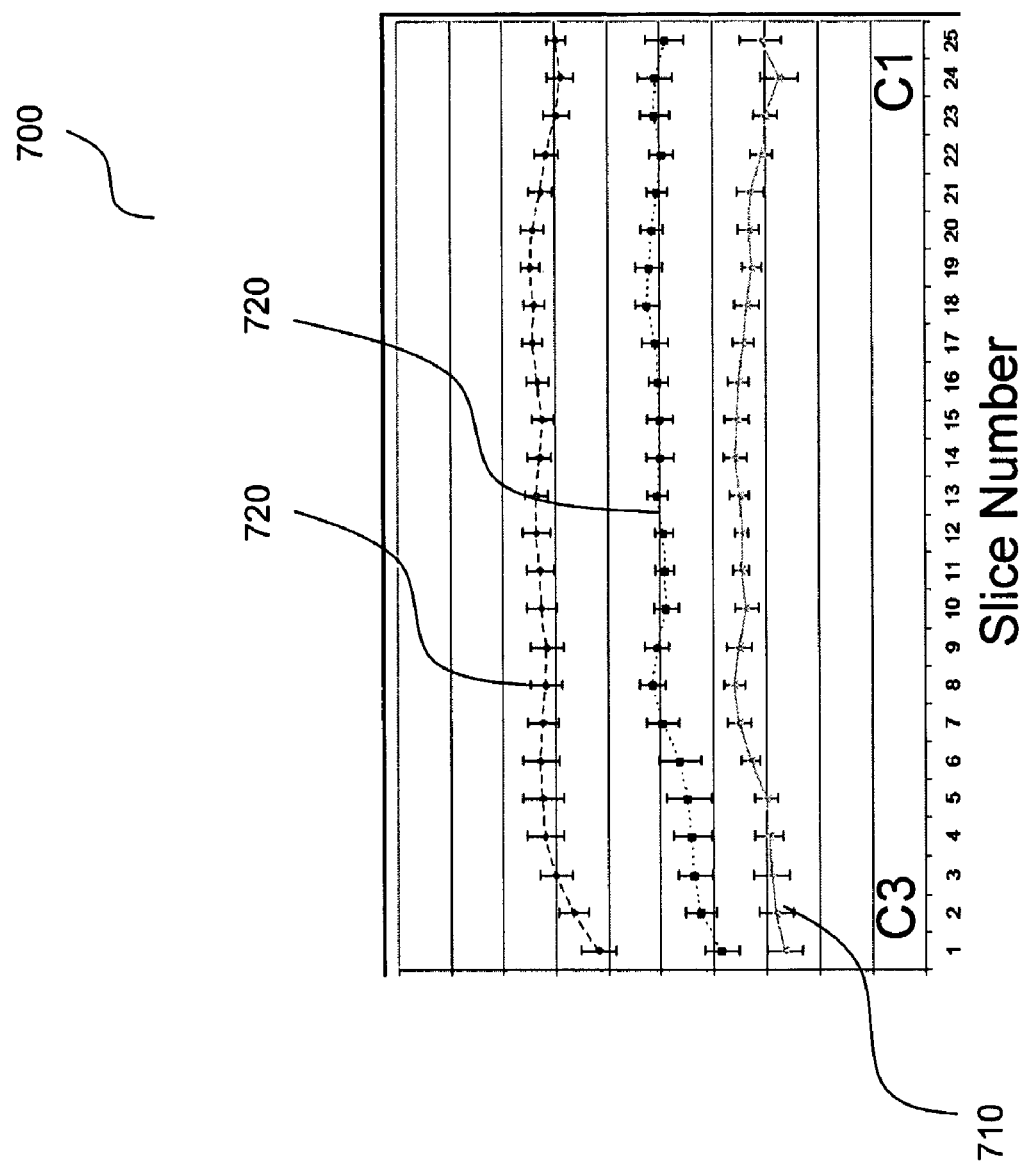
FIG. 7 illustrates an exemplary curve comparing dorsal column MTCSF values at different stages of disease to the control values, whereby control values may be encoded as a lookup table for determining slice dependence of identified abnormality.

FIG. 7 illustrates an exemplary MTCSF plot 700 of a selected region as a function of image slice along the spinal cord. Exemplary plot 700 includes a control plot 710, a plot indicating mildly symptomatic AMN 715, and an advanced stage of AMN 720. For a given patient, successive MRI clinical procedures are performed, MTCSF values corresponding to a selected region may be displayed corresponding to successive clinical sessions, allowing the clinician to quantitatively assess the state of demyelination for a given MRI session, and to quantitatively track the progression of the disease in the patient.

Although the above discussion pertains to the use of CSF as a reference for generating quantitative MTw or so-called MTCSF images of the spinal cord that can be compared between subjects or longitudinally, it will be readily apparent that the present invention may be used with other anatomical components having minimal MT effects, such as blood or urine, serving as the reference. Accordingly, the present invention may use other references within an RF saturation image to identify a reduction or breakdown of macromolecular components within a given tissue, e.g. benign prostatic hyperplasia (BPH), or inflammatory bowel disease (IBD).

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for quantifying loss of macromolecular components in tissue, comprising:

acquiring an MTw image of the tissue, the MTw image having a plurality of voxels, wherein each voxel has a corresponding MR signal;

identifying a reference region of voxels within the plurality of voxels, wherein the region of voxels corresponds to a reference material having a minimal magnetization transfer effect;

computing a reference MR signal corresponding to the region of voxels; and computing a normalized MT weighted image, based on the ratio of the MTw image and the reference MR signal.

2. The method of claim 1, wherein computing the reference MR signal comprises computing an average of a plurality of MR signals corresponding to the region of voxels.

3. The method of claim 1, wherein acquiring the MTw image comprises employing an image acquisition scheme with an MT preparation pre-pulse.

4. The method of claim 1, wherein acquiring the MTw image comprises employing a T2* weighted pulse sequence with an MT pre-pulse.

5. The method of claim 1, wherein the tissue comprises spinal cord tissue.

6. The method of claim 5, wherein the reference material comprises cerebrospinal fluid.

7. The method of claim 1, wherein computing the normalized MT weighted image comprises dividing each MTw signal by the reference MR signal.

8. The method of claim 1, further comprising:
  acquiring a second MR image; and
  comparing the second MR image with the MT weighted image.

9. An MRI system, comprising:
  a main magnet;
  a gradient coil;
  an RF coil; and
  a computer having a computer readable medium encoded with a program for acquiring an MTw image of the tissue, the MTw image having a plurality of voxels, wherein each voxel has a corresponding MR signal; identifying a reference region of voxels within the plurality of voxels, wherein the region of voxels corresponds to a reference material having a minimal magnetization transfer effect; computing a reference MR signal corresponding to the region of voxels; and computing an MTCSF image, based on the MR image and the reference MR signal.

10. The MRI system of claim 9, wherein the program for computing the reference MR signal comprises a program for computing an average of a plurality of MR signals corresponding to the reference region of voxels.

11. The MRI system of claim 9, wherein the program for computing the MTCSF image comprises a program for dividing each MTw signal by the reference MR signal.

12. A method for quantifying demyelination in a spinal cord, comprising:
  acquiring an MTw image of the spinal cord, the MTw image having a plurality of voxels, wherein each voxel has a corresponding MR signal;
  identifying a reference region of voxels within the plurality of voxels, wherein the region of voxels corresponds to cerebrospinal fluid;
  computing a reference MR signal corresponding to the region of voxels; and
  computing a normalized MT weighted image, based on the ratio of the MTw image and the reference MR signal.

13. The method of claim 12, further comprising identifying a hyperintensity signal region within a portion of the spinal cord that corresponds to white matter.

14. The method of claim 12, further comprising:
  acquiring a conventional MR image of the spinal cord; and
  comparing the normalized MT weighted image with the conventional MR image.

15. The method of claim 14, wherein comparing the normalized MT weighted image comprises co-registering the conventional MR image and the normalized MT weighted image.

* * * * *